United States Patent
Pomerantzeff

[11] 4,061,423
[45] Dec. 6, 1977

[54] ILLUMINATION SYSTEM FOR OPHTHALMOSCOPE

[75] Inventor: Oleg Pomerantzeff, Brookline, Mass.

[73] Assignee: Retina Foundation, Boston, Mass.

[21] Appl. No.: 670,701

[22] Filed: Mar. 26, 1976

Related U.S. Application Data

[63] Continuation-in-part of Ser. No. 536,879, Dec. 27, 1974, Pat. No. 3,954,329, which is a continuation-in-part of Ser. No. 292,150, Sept. 25, 1972, and Ser. No. 512,327, Oct. 4, 1974, Pat. No. 3,944,341.

[51] Int. Cl.² ............................. A61B 3/14; G02B 5/16
[52] U.S. Cl. ..................... 351/16; 350/96 B; 351/6; 351/7
[58] Field of Search ................ 351/6, 7, 16; 350/96 B

[56] References Cited

U.S. PATENT DOCUMENTS

| | | | |
|---|---|---|---|
| 1,605,725 | 11/1926 | Herbert, Jr. | 351/7 |
| 3,630,602 | 12/1971 | Herbert | 351/16 |
| 3,770,342 | 11/1973 | Dudragne | 351/7 |

Primary Examiner—Paul A. Sacher
Attorney, Agent, or Firm—Kenway & Jenney

[57] ABSTRACT

Disclosed are improvements in an illuminating system for an ophthalmoscope of the type employing transillumination through the sclera of the eye. One or more fiber optic bundles convey light from a source to the sclera. Each fiber optic bundle has a physically separated tip portion of relatively small size (e.g., less than one inch long) and mass supported in a fitting. The tip portion is biased in a direction away from the main fiber optic bundle, is optically aligned therewith, and has a maximum separation therefrom of approximately 0.160 inch (4 mm). With this arrangement, a light biasing force applied to the tip portion can absorb any movement of the tip portion as it is placed in contact with the eye. The small force thus applied to the eye, even if there is minor over-exertion of pressure by the instrument operator, reduces the possibility of damage to the eye.

19 Claims, 2 Drawing Figures

ILLUMINATION SYSTEM FOR OPHTHALMOSCOPE

CROSS REFERENCE TO RELATED APPLICATIONS

This application is a continuation-in-part of my co-pending application Ser. No. 536,879, filed Dec. 27, 1974 entitled "Wide-Angle Ophthalmoscope Employing Transillumination", (now U.S. Pat. No. 3,954,329) which was itself a continuation-in-part of my previous application Ser. No. 292,150, filed Sept. 25, 1972 entitled "Wide-Angle Ophthalmoscope" and of my previous application Ser. No. 512,327, filed Oct. 4, 1974, entitled "Wide-Angle Ophthalmoscope and Fundus Camera", (now U.S. Pat. No. 3,994,341) all of which are assigned to the assignee hereof. Filed concurrently herewith is another patent application of mine directed to an "Ophthalmoscope with Uniform Illumination".

BACKGROUND OF THE INVENTION

This invention relates to an ophthalmoscope, i.e., an instrument for viewing the interior of the human eye. More particularly, the invention provides an improved illumination system for an ophthalmoscope serving to provide adequate illumination for the diagnostic purposes of the ophthalmoscope, while minimizing the risk of damage to the eye and discomfort to the patient.

Accordingly, it is the object of this invention to provide such a system for illuminating the interior of the eye that has less chance of damaging the eye, or causing discomfort to the patient, than has been heretofore possible.

Other objects of the invention will in part be obvious and will in part appear hereinafter.

BRIEF DESCRIPTION OF THE DRAWINGS

For fuller understanding of the nature and objects of the invention, reference should be made to the following detailed description and the accompanying drawings in which.

SUMMARY OF THE INVENTION

The examination of an eye with a wide-angle ophthalmoscope, particularly of the type disclosed in the above-noted application Ser. No. 536,879, involves contact with the human eye. Thus, despite the general high level of skill of the users of such instruments and despite the common use of anesthetics in the eye to be examined, it is highly desirable that the instrument be designed to minimize the pressure applied to the eye, either with normal use of the instrument or through miscalculation by the user. The most recent generation of ophthalmoscopes, as described in the above-mentioned U.S. Patent Application Ser. No. 536,879, employs a form of illumination of the interior of the eye requiring actual contact with the sclera by one or more end surfaces of fiber optic bundles. According to the present invention, improvements in the illumination system are provided which minimize the pressure whether intentional or accidental, applied to the sclera by the illumination system. To accomplish this, the conventional fiber optic bundle, or bundles, that convey the light from a light source to the surface of the eye are terminated in a fitting a short distance (e.g., less than an inch) from the actual surface of the eye. A short segment of a similar fiber optic bundle, biased toward an eye-contacting position, is disposed between the main bundle and the sclera. With this arrangement, of course, the biasing need only accommodate the relatively small minute mass of the short segment of fiber optic bundle. The resultant force on the eye can thus be substantially diminished.

DESCRIPTION OF ILLUSTRATED EMBODIMENT

Figure 1:
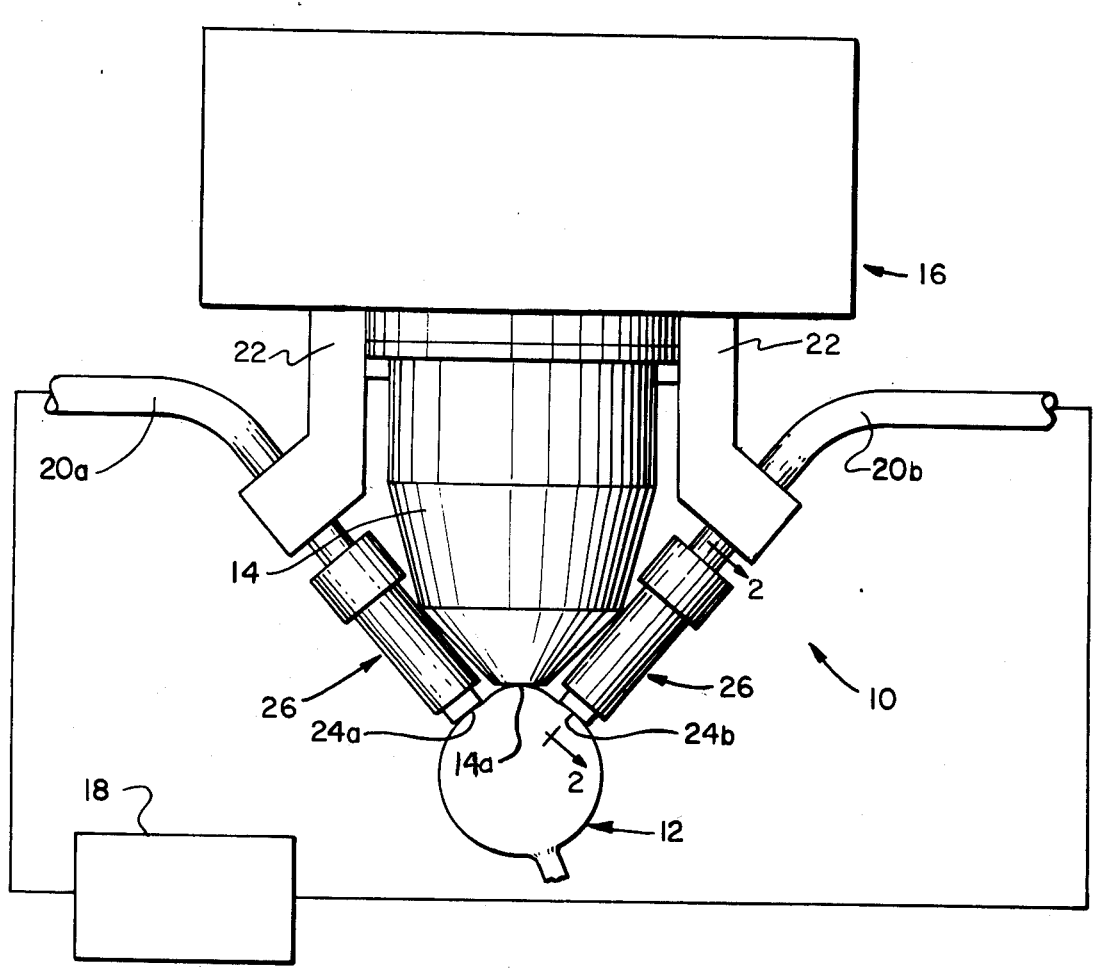
FIG. 1 is a somewhat schematic, plan view of a transillumination type ophthalmoscope operatively positioned on an eye.

FIG. 1 illustrates a wide-angle ophthalmoscope 10 operatively disposed contacting the human eye, indicated generally at 12. The ophthalmoscope includes a central tapered housing 14 that incorporates optical elements designed to produce an image of the eye's fundus, and a larger housing 16 to which a camera can be mounted on the opposite side from the housing 14 for photographing the image of the fundus. The optical elements in housing 14 include a fixedly secured contact lens which has a surface 14a that is placed contiguous with the eye 12 for viewing the fundus. These elements are described in further detail in the above-noted application filed on even date herewith.

Illumination of the fundus of the eye 12 for viewing, photographing, etc. if provided by an illumination system comprising a light source 18 that delivers light to one end of each of a pair of flexible fiber optic bundles 20a and 20b. Near the ends remote from the light source 18, the bundles 20a and 20b are supported by brackets 22 secured to the housing 14. In a typical arrangement, the location of the support of bundles 20a and 20b by the brackets 22 is between one and two inches from the face 24a and 24b that contact the exterior of the eye 12. The theory and technique of illumination of the fundus, and the preferred location on the eye 12 for placement of the exit facets 24a and 24b, are as described in the above-mentioned co-pending application Ser. No. 536,879, which is incorporated herein by reference. Beyond its point of support by its respective bracket 22, each bundle 20a and 20b enters a receptacle 26.

The opthalmoscope 10 thus has a lens surface 14a and at least one and preferably two illuminating surfaces 24a and 24b which contact, i.e., physically abut, different locations on the eye 12 being examined. These multiple regions of contact with the eye require careful location in order to illuminate and view the fundus correctly. However, eyes differ sufficiently in shape and size to preclude the use of a fixed geometry for the surfaces 14a, 24a and 24b. Instead, they must be adjustable relative to one another. As will now be described, the invention provides such an adjustable mounting structure which attains the foregoing multiple surface contact with minimal risk of discomfort or damage to the patient by undue pressure on the eye 12.

Figure 2:
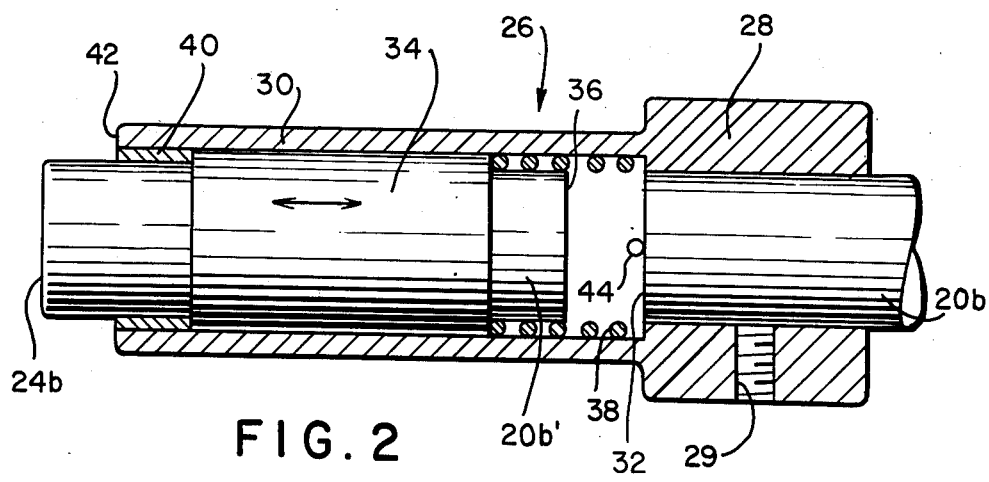
FIG. 2 is a sectional view taken at 2—2 of FIG. 1.

Referring to FIG. 2, each receptacle 26, which provides the desired adjustable mounting of one surface 24a, 24b, has a relatively short tubular base 28 and a relatively longer tubular slide portion 30. The receptacle has a cylindrical passage extending through it, with different diameters as shown. The fiber optic bundle 20b is telescopically received in the passage within the base 28 and is secured therein in any conventional fashion (e.g., cement, a set screw in a threaded opening 29, etc.). The terminal facet 32 of the fiber optic bundle 20b is perpendicular to the common longitudinal, optical axis of the bundle 20b and of the receptacle 26. (In certain circumstances it may be desirable to provide a slight convexity of the surface 32, in order to maximize the transmission of light from the bundle 20b across an air gap to the bundle 20b'. Such a slight modification of surface 32 would in no way change the construction or operation of other portions of the apparatus.)

A slide member 34 is disposed for sliding motion within the cylindrical passage of the tubular portion 30 and carries a short (e.g., 0.875 inch) length of fiber optic bundle 20b' coaxially seated therein. The terminal surface 24b, referred to above in connection with FIG. 1, is the exit facet of the fiber optic bundle portion 20b'. The input facet 36 of the fiber optic bundle 20b' is transverse to the aforementioned optical axis and hence is parallel to the facet 32 when both facets are planar. The bundle 20b' is separated from the bundle 20b and is spaced from it along the optical axis by an air gap. By way of example, this gap normally has a maximum width, i.e., spacing between the facets 32 and 36, of 4 mm.

A spring 38, disposed within the slide portion 30 between the base 28 and the slide 34 biases the slide 34, and hence the fiber optic bundle 20b', toward a position of maximum separation (i.e., the aforementioned 4 mm gap) from the facet 32 of the fiber optic bundle 20b. The maximum biased position of slide 34 is fixed by a retaining ring 40, preferably an optically dark and smooth low friction sleeve, secured in the passage of the slide portion 30 adjacent its end 42. The ring 40 preferably has a wall thickness that is less than that of the slide 34 in order not to interfere with the movement of bundle 20b'. In order to facilitate smooth movement of the slide 34, which is a rather close fit within the slide portion 30, a vent hole 44 is provided in the cylindrical portion adjacent the base 28.

Preferably, the terminal facet 24b is spaced longitudinally along the axis of the receptacle 26 away from the receptacle end 42 by an amount approximately equal to the maximal separation of faces 32 and 36 (e.g., about 4 mm). With a suitable choice of the biasing spring 38, movement of the slide 34 can be limited to an amount less than the separation between facets 32 and 36 (i.e., an appropriate choice of wire size and convolution separation for the spring 38 will assure that all adjacent convolutions are in contact, thereby preventing further collapse of the spring, before the surface 36 reaches the surface 32). This arrangement assures that the terminal facet 24b is not pushed back to the plane of receptacle end 42, in which position the receptacle itself would contact the eye, which is undesirable.

The receptacle 26 thus provides a light conductor, i.e., the short bundle 20b', of small mass, and mounted for movement along the optical axis with such low friction and low spring bias, that the conductor telescopes into the passage of the bracket upon engagement of the exit facet 24b against the eye 12. Similarly, the light conductor telescopes outward to maintain contact of the facet 24b with the eye. This adjustment movement of the light conductor occurs under such light force that it does not cause discomfort, much less injury, to the patient. The spring 38 is chosen, relative to the area of facet 24b, such that the pressure exerted on an eye is no greater than intraocular pressure (i.e., about 20 mm. of mercury).

Normally, in a light transmission system, one would attempt to avoid an air gap, such as that shown in FIG. 2 between the facets 32 and 36. In accordance with the present invention, however, it has been found that adequate illumination of the eye is obtainable even with the provision of the air gap. Furthermore, the safety benefits in providing a separate tip portion 20b' of the light conduit, which is of small size and mass, far outweigh any light loss attendant such a construction.

In use, the device 10 is moved from a remote position to that shown in FIG. 1, where the lens surface 14a and the facets 24a and 24b are in contact with the patient's eye 12. Even with a skilled operator, damaging or painful pressure on the eye could result if the device 10 lacked the low mass and low force adjustment structure illustrated in FIG. 2. Without that structure, the three point contact with the eye could not adjust to accommodate eye of different shape.

It will thus be appreciated by those skilled in the art that the following features of the present invention contribute to a safer eye illumination system: the small size and weight of the light conduit 20b' that actually contacts the eye; the free slidability of conduit 20b' in the receptacle 26; the slight biasing force of spring 38; and the venting of receptacle 26 through conduit 20b'.

For clarity of description the invention has been described in terms of an ophthalmoscope. As noted above, this term is used herein with reference to any device for examining (including recording) an eye fundus. Hence the device 10 illustrated and described herein can be part of a fundus camera, or of another instrument which is used for viewing, recording or otherwise examining an eye fundus.

It will be thus be seen that the objects set forth above, among those made apparent from the preceding description, are efficiently attained. Since certain changes may be made in the above construction without departing from the scope of the invention, it is intended that all matter contained in the above description or shown in the accompanying drawings be interpreted as illustrative and not in a limiting sense.

It is also to be understood that the following claims are intended to cover all the generic and specific features of the invention herein described, and all statements of the scope of the invention, which as a matter of language, might be said to fall therebetween.

Having described the invention, what is claimed as new and secured by Letters Patent is:

1. In a device for optically examining an eye and having eye illuminating means and viewing means, said eye illuminating means including a light conduit having an exit facet for contact with the eye, the improvement comprising receptacle means supportingly mounting said light conduit for movement along an optical path, biasing means for biasing said light conduit toward a first position relative to said receptacle means in which said exit facet is exterior of said receptacle, said light conduit having a light entrance facet disposed within said receptacle means and means in said illumination means stationary relative to said movement of said light conduit for radiating light onto said entrance facet within said receptacle means.

2. In a device according to claim 1, the further improvement wherein means are provided limiting said light conduit to a maximum movement, with respect to said receptacle.

3. In a device according to claim 1, the further improvement wherein said receptacle has an internal bore, said light conduit being supported in slide member being sized for sliding movement in said bore, said receptacle further including retaining means positioned to abut said slide, thereby to retain said slide within said bore and to define said first position of said light conduit.

4. In a device according to claim 3, the further improvement wherein said retaining means comprises a ring secured in said internal bore having a wall thickness less than the wall thickness of said slide.

5. In a device according to claim 3, the further improvement wherein said internal bore includes an annular shoulder at the opposite end of said bore from said retaining means, and wherein said biasing means comprises a compression spring bearing at opposite ends against said annular shoulder and against an annular face of said slide.

6. In a device according to claim 5, the further improvement wherein the longitudinal spacing along said internal bore, from said annular shoulder to said light entrance facet of said light conduit is substantially equal to the longitudinal spacing along the axis of said light conduit from said exit facet to the nearest end of said receptacle, when said light conduit is in said first position.

7. In a device according to claim 6, the further improvement wherein each said spacing, when said light conduit is in said first position, is approximately 4 mm.

8. In a device according to claim 5, the further improvement wherein a vent opening through a wall of said receptacle is provided from said cylindrical bore to the exterior of said receptacle at a longitudinal location adjacent said annular shoulder.

9. In a device according to claim 8, the further improvement wherein said means for radiating light onto said entrance facet comprise a light source remote from said receptacle and a second light conduit having a first end facet positioned to receive light from said light source and a second end facet disposed within said receptacle and aligned with said entrance facet.

10. In a device according to claim 9, the further improvement wherein said second end facet is separated from said entrance facet by a distance of approximately 4 mm from said entrance facet by a distance of approximately 4 mm when said light conduit and slide are in said first position.

11. In a device according to claim 10, the further improvement wherein each said light conduit comprises a fiber optic bundle.

12. In a device according to claim 1, the further improvement where in said light conduit has a length of less than an inch.

13. In a device according to claim 12, the further improvement wherein said light conduit is cylindrical and has a diameter of approximately one-quarter inch.

14. In an ophthalmoscope having a contact lens for viewing an eye fundus and having illuminating means for directing light onto the eye sclera for illumination therethrough of the eye fundus, the improvement comprising
A. first means in said illuminating means for projecting fundus-illuminating light,
B. optical conductor means in said illuminating means and having opposed facets, a first in optical alignment across on air gap with said first means for receipt of projected fundus-illuminating light and a second arranged for placement in contact with an eye sclera for directing such light onto the sclera, and
C. means mounting said lens together with said first means and said optical conductor means, said mounting means mounting said optical conductor means in said optical alignment and for facile movement relative to said first means upon engagement of said second facet with an eye sclera.

15. In an ophthalmoscope having a contact lens for viewing an eye fundus and having illuminating means for directing light onto the eye sclera for illumination therethrough of the eye fundus, the improvement comprising
A. optical conductor means in said illuminating means and having opposed facets, a first for the receipt of projected fundus-illuminating light and a second arranged for placement in contact with an eye sclera for directing such light onto the sclera,
B. means for mounting said lens and for mounting said optical conductor means, said mounting means mounting said optical conductor means for facile movement along an optical path and relative to said lens upon engagement of said second facet with an eye sclera, and
C. means in said illuminating means mounted with said mounting means in stationary disposition along said optical path relative to said optical conductor means, and in optical alignment along said optical path for projecting fundus-illuminating light onto said first facet.

16. In an opthalmoscope according to claim 15, the further improvement comprising means forming an air gap along said optical path between said first facet of said optical conductor means and said light-projecting means, and across which said projecting means transfers fundus-illuminating light to said first facet of said conductor means.

17. In an ophthalmoscope according to claim 15, the further improvement wherein said mounting means mounts said optical conductor means with said first facet spaced by an air gap from said light-projecting means, and wherein said movement of said optical conductor means change the width of said gap.

18. In an ophthalmoscope according to claim 16, the further improvement comprising resilient bias means urging said optical conductor means for movement relative to said mounting means in a direction to increase the space between said first facet and said light-projecting means.

19. In an ophthalmoscope according to claim 17, the further improvement wherein
A. said conductor means includes a fiber optic bundle the facets of which form said first and second facets, and
B. said mounting means includes tubular support means fixed relative to at least one of said lens and said light-projecting means and telescopically seating at least a portion of said bundle for sliding motion relative thereto.

* * * * *